(12) United States Patent
Murray

(10) Patent No.: US 6,274,130 B1
(45) Date of Patent: Aug. 14, 2001

(54) HAIR CONDITIONING COMPOSITION

(75) Inventor: Andrew Malcolm Murray, South Wirral (GB)

(73) Assignee: hesebrough-Pond's USA Co., division of Conopco, Inc., Greenwich, CT (US)

( * ) Notice: Subject to any disclaimer, the term of this patent is extended or adjusted under 35 U.S.C. 154(b) by 0 days.

(21) Appl. No.: 08/399,395

(22) Filed: Mar. 6, 1995

(30) Foreign Application Priority Data

Mar. 9, 1994 (GB) ................................... 9404550

(51) Int. Cl.⁷ ...................................... A61K 7/075
(52) U.S. Cl. ........................................... 424/70.12
(58) Field of Search ................ 424/78.08, 70.12

(56) References Cited

U.S. PATENT DOCUMENTS

| | | |
|---|---|---|
| 2,891,920 | 6/1959 | Hyde et al. . |
| 3,294,725 | 12/1966 | Findlay et al. . |
| 3,360,491 | 12/1967 | Axon . |
| 4,724,851 * | 2/1988 | Cornwall et al. .................... 132/203 |
| 4,874,416 | 10/1989 | Yokokawa et al. . |
| 4,902,499 * | 2/1990 | Bolish, Jr. et al. ............... 424/70.12 |
| 4,950,468 | 8/1990 | Nakamura et al. . |
| 4,983,418 * | 1/1991 | Murphy et al. ................... 424/70.31 |
| 5,085,857 * | 2/1992 | Reid et al. ........................... 514/937 |
| 5,246,694 * | 9/1993 | Birthwistle ....................... 424/70.12 |
| 5,334,376 * | 8/1994 | Robbins et al. .................... 514/937 |

FOREIGN PATENT DOCUMENTS

| | | |
|---|---|---|
| 0 268 982 | 6/1988 | (EP) . |
| 0 285 364 | 10/1988 | (EP) . |
| 0 460 683 | 12/1991 | (EP) . |
| 0 529 883 | 3/1993 | (EP) . |
| WO 92/09264 | 6/1992 | (WO) . |
| WO 93/19723 | 10/1993 | (WO) . |

OTHER PUBLICATIONS

Wendel, S.R. and diSapio, A.J.: Cosmetics & Toiletries, vol. 98, May 1983, pp. 103–106.

* cited by examiner

*Primary Examiner*—Peter F. Kulkosky
(74) *Attorney, Agent, or Firm*—Milton L. Honig

(57) ABSTRACT

A rinse off hair conditioning composition comprising:
(a) about 0.05 to about 5% by weight of cationic surfactant,
(b) 0.01 to 10% by weight of an emulsion polymerised dimethiconol nonionic conditioning polymer having the formula:

$$HO-Si(CH_3)_2-O-[Si(CH_3)_2-O-]_n Si(CH_3)_2-OH$$

where n is greater than 2700, and
(c) water. The invention also comprises a method of making a conditioning composition.

9 Claims, No Drawings

HAIR CONDITIONING COMPOSITION

BACKGROUND OF THE INVENTION

1. Field of the Invention

This invention relates to hair conditioning compositions intended to be rinsed off and containing non-volatile insoluble silicone gum, particularly dimethiconol gum.

2. The Related Art

Use of high viscosity gums as hair conditioning agents is known and suitable gums are described in U.S. Pat. No. 4,152,416 (Spitzer). The gums are usually used in solution in a volatile silicone such as a cyclomethicone.

Emulsion polymerised silicones are known from U.S. Pats. No. 2,891,920 (Hyde), 3,294,725 (Findlay), and 3,360,491 (Axon).

Emulsion polymerised dimethylpolysiloxane microemulsions are described in EP 0 268 982 (Toray). Dimethiconol materials are taught as one of a range of possibilities.

Articles such as "Organofunctional Silicones for Personal Care Applications", Wendel, Samuel R and DiSapio, Alfred J. *Cosmetics & Toiletries* vol 98 May 1983, pp 103–106 have taught away from the use of Dimethiconol in hair compositions.

Dimethiconol can be prepared in various ways, one of which is emulsion polymerisation.

Silicone oils are often added to hair conditioning compositions in the form of aqueous emulsions. These emulsions are usually formed by mechanical shearing of the oil. Sometimes they are formed by chemical emulsification but this is not the same as emulsion polymerisation and does not provide the unexpected advantages of the present invention.

A problem with prior hair conditioning compositions has been that they either provide inadequate conditioning; or the use of high viscosity gums leads to processing difficulties. The latter problem has in the past been partially solved by the use of solvent for the gum. Such solvents are undesirable for the consumer and affect the conditioning properties of the gum.

SUMMARY AND DETAILED DISCUSSION OF THE INVENTION

According to the present invention a hair conditioning composition which is substantially free from anionic surfactant comprises:

(a) about 0.05 to about 5% by weight cationic surfactant,
(b) 0.01 to 10% by weight of an emulsion polymerised dimethiconol nonionic conditioning polymer having the formula:

$$HO-Si(CH_3)_2-O-[Si(CH_3)_2-O-]_nSi(CH_3)_2-OH$$

where n is 2700 or more to give a molecular weight of over 200,000, and
(c) water.

Substantially free from anionic surfactant means that the composition contains less than 1% of anionic surfactant.

The composition preferably also comprises about 0.2 to about 20% by weight of a long chain fatty alcohol.

Preferably the average particle size of the dimethiconol polymer is less than 20 microns and more preferably it is less than 2 microns. Small particle size enables a more uniform distribution of silicone conditioning agent on the hair for the same concentration of silicone in the shampoo.

The polymer can be cross-linked. Advantageously the viscosity of the dimethiconol lies in the range 1–20 million cst because higher viscosity increases the conditioning effect obtainable from the silicone.

The cationic surfactant is preferably present in an amount of 0.1 to 1% by weight. Mono-, di- and tri-alkyl substituted quaternary ammonium cationic surfactants may be used; also ethoxylated quaternary ammonium cationic surfactants. Suitable cationic surfactants include: Cetyl trimethyl ammonium chloride, Behenyl trimethyl ammonium chloride, Stearyl dimethylbenzyl ammonium chloride, cetylpyridinium chloride, and materials given the CTFA designations: Quaternium-5, Quaternium-31, Quaternium-18, and mixtures thereof. The preferred cationic surfactants are Cetyl trimethyl ammonium chloride and behenyl trimethyl ammonium chloride.

Long chain fatty alcohols may have fatty alkyl or alkenyl chains with 14 to 22 carbon atoms, preferably 16 to 20. Fatty alcohol which is particularly suitable for use in conjunction with cationic surfactant is a mixture of cetyl and stearyl alcohols. Preferably the composition comprises 0.5 to 10% by weight of long chain fatty alcohol, most preferably from 1 to 5% by weight.

The composition may also contain optional nonionic and amphoteric surfactant.

The nonionic surfactants suitable for use in the composition of the invention may include condensation products of aliphatic ($C_8$–$C_{18}$) primary or secondary linear or branched chain alcohols or phenols with alkylene oxides, usually ethylene oxide and generally 6–30 EO.

Other suitable nonionics include mono or di alkyl alkanolamides or alkyl polyglucosides. Examples include coco mono or diethanolamide, coco mono isopropanolamide, and coco di glucoside.

The amphoteric surfactants suitable for use in the composition of the invention may include alkyl amine oxides, alkyl betaines, alkyl amidopropyl betaines, alkyl sulphobetaines, alkyl glycinates, alkyl carboxyglycinates, alkyl amphopropionates, alkyl amidopropyl hydroxysultaines, acyl taurates and acyl glutameates wherein the alkyl and acyl groups have from 8 to 18 carbon atoms. Examples include lauryl amine oxide, cocodimethyl sulphopropyl betaine and preferably lauryl betaine, cocamidopropyl betaine and sodium cocamphopropionate.

The composition may also include minor amounts of other ingredients such as antibacterial agents, foam boosters, pearlescers, perfumes, dyes, colouring agents, preservatives, thickeners, proteins, polymers, phosphate esters and buffering agents.

The invention also comprises a method for preparation of a conditioning composition which contains insoluble silicone having a molecular weight above 200,000 and a viscosity of greater than 1 million cst as the conditioning agent comprising the steps of forming the silicone into an emulsion, the emulsion having a viscosity of less than 1000 cps, then mixing the emulsion with the other ingredients. Preferably the emulsion comprises greater than 40% by weight of the silicone.

In a preferred method the silicone is emulsion polymerised because such a material is able to combine small particle size with high viscosity.

Dimethiconol silicone is particularly preferred. The dimethiconol silicone can either be used as such or it can be end-capped with a further methyl group.

The invention will now be further described with reference to the following examples:

TABLE 1

|                    | A   | B   | 1   | 2   | 3   | 4   | 5   |
|--------------------|-----|-----|-----|-----|-----|-----|-----|
| CTAC[1]            | 0.7 | 0.7 | 0.7 | 0.7 | 0.5 | 0.7 | —   |
| BTAC[2]            | —   | —   | —   | —   | —   | —   | 0.7 |
| Laurex CS[3]       | 1.9 | 1.9 | 1.9 | 3.5 | 1.0 | 1.9 | 1.9 |
| Paraffin Wax       | 1.0 | 1.0 | 1.0 | 1.0 | —   | 1.0 | 1.0 |
| Glycerol monostearate | 0.7 | 0.7 | 0.7 | 0.7 | —   | 0.7 | 0.7 |
| Natrosol 250 HR[4] | —   | —   | —   | —   | 1.3 | —   | —   |
| Polysurf 67[5]     | —   | —   | —   | —   | —   | 0.2 | —   |
| X2-1766[6]         | —   | —   | 1.7 | —   | 3.3 | —   | 2.5 |
| X2-1784[7]         | —   | —   | —   | 2.0 | —   | 6.0 | —   |
| BY 22-026[8]       | —   | 2.0 | —   | —   | —   | —   | —   |
| minors             |     |     |     |     |     |     |     |
| water              | as required to 100% | | | | | | |

[1] is Cetyl trimethyl ammonium chloride
[2] is behenyl trimethyl ammonium chloride
[3] is 2:1 hexadecanol:octadecanol ex Albright & Wilson
[4] is hydroxy ethyl cellulose ex Hercules
[5] is cetyl hydroxyethyl cellulose ex Hercules
[6] is a 60% silicone emulsion polymer, mol wt 300,000
[7] is a 50% silicone emulsion polymer, mol wt 240,000
[8] is a 50% mechanical emulsion of silicone, mol wt 115,000

The compositions detailed in Table 1 were used to treat identical hair switches which were then subjected to a series of paired comparison tests by trained panellists. The two attributes considered to be most indicative of conditioning benefit are (a) ease of dry combing and (b) smooth feel of the hair when dry. In each case the comparison was with the comparative example A which contained no silicone conditioning agent. Comparative Example B, containing a mechanical emulsion of silicone conditioning agent according to the prior art, did not give rise to any statistically significant differences. Whereas all the compositions according to the invention were statistically preferred over Comparative Example A. From these comparative tests it can be concluded that compositions according to the invention and prepared according to the method of the invention give superior results to the mechanical silicone emulsion composition B.

What is claimed is:

1. A rinse off hair conditioning composition substantially free from anionic surfactant comprising:
    (a) about 0.05 to about 5% by weight of cationic surfactant,
    (b) 0.01 to 10% by weight of an emulsion polymerized dimethiconol nonionic conditioning polymer with viscosity in the range 1 to 20 million cst and having the formula:

where n is greater than 2700, and
    (c) water.

2. A composition according to claim 1 wherein the average particle size of the dimethiconol polymer is less than 20 microns.

3. A composition according to claim 2 wherein the average particle size of the dimethiconol polymer is less than 2 microns.

4. A composition according to claim 1 wherein the viscosity of the dimethiconol lies in the range 1–20 million cst.

5. A composition according to claim 1 which further comprises 0.2 to 20% by weight of a $C_{14-22}$ alcohol.

6. A composition according to any preceding claim wherein the cationic surfactant is selected from the group comprising cetyl trimethyl ammonium chloride and behenyl trimethyl ammonium chloride.

7. A method for preparation of a rinse off conditioning composition which comprises a cationic surfactant and insoluble silicone which is a dimethiconol polymer having a molecular weight above 200,000 and a viscosity of greater than 1 million cst as conditioning agent comprising the steps of forming the silicone into an emulsion, the emulsion having a viscosity of less than 1000 cps, then mixing the emulsion with the cationic surfactant.

8. A method as claimed in claim 7 wherein the emulsion comprises more than 40% by weight of the silicone.

9. A method according to claim 7 wherein the silicone is emulsion polymerised dimethiconol.

* * * * *

UNITED STATES PATENT AND TRADEMARK OFFICE
CERTIFICATE OF CORRECTION

PATENT NO.    : 6,274,130 B1
DATED         : August 14, 2001
INVENTOR(S)   : Murray It is certified that error appears in the above-identified patent and that said Letters Patent is hereby corrected as shown below:

<u>Title page,</u>
Item [73], please change Assignee from "hesebrough-Ponds's USA Co., division of Conopco, Inc." to -- Chesebrough-Pond's USA Co., Division of Conopco, Inc. --

Signed and Sealed this

Sixth Day of August, 2002

Attest:

JAMES E. ROGAN
Attesting Officer    Director of the United States Patent and Trademark Office